United States Patent [19]

Harrison et al.

[11] 3,996,105

[45] Dec. 7, 1976

[54] MIXED METHANE-UTILIZING CULTURES FOR PRODUCTION OF MICRO-ORGANISMS

[75] Inventors: David E. F. Harrison, Faversham; John H. Harwood; Barry N. Herbert, both of Sittingbourne, all of England

[73] Assignee: Shell Oil Company, Houston, Tex.

[22] Filed: Jan. 6, 1975 (Under Rule 47)

[21] Appl. No.: 539,202

[30] Foreign Application Priority Data

Jan. 7, 1974 United Kingdom ............... 678/74

[52] U.S. Cl. .............................. 195/28 R; 195/111
[51] Int. Cl.² .......................................... C12B 1/00
[58] Field of Search ................. 195/111, 115, 28 R, 195/49, 81, 82, 96

[56] References Cited

UNITED STATES PATENTS

| | | | |
|---|---|---|---|
| 3,767,534 | 10/1973 | Miura | 195/111 |
| 3,834,989 | 9/1974 | Harrison | 195/123 X |

FOREIGN PATENTS OR APPLICATIONS 45-36,156  11/1970  Japan ............... 195/111

OTHER PUBLICATIONS

Clifton et al. "Metabolism of Single Carbon Compounds" Annual Reviews of Microbiology 1970 pp. 135–147

*Primary Examiner*—A. Louis Monacell
*Assistant Examiner*—R. B. Penland

[57] ABSTRACT

A process for the production of micro-organisms in which a methane-utilising micro-organism is grown under aerobic conditions in the presence of (a) one or more methanol-utilising micro-organisms which is/are capable of metabolising methanol produced by the growing methane-utilising micro-organisms, and (b) one or more non-methylotropic micro-organisms which is/are capable of metabolising organic substances produced by the methane and/or methanol-utilising micro-organisms.

4 Claims, No Drawings

MIXED METHANE-UTILIZING CULTURES FOR PRODUCTION OF MICRO-ORGANISMS

BACKGROUND OF THE INVENTION

This invention relates to a process for the production of micro-organisms. Many micro-organisms are known which can utilise hydrocarbons or certain oxygenated or other derivatives thereof as their carbon and/or energy source. The dried biomass obtainable by the cultivation of such micro-organisms, often referred to as single cell protein, is rich in protein and can be used as a possible foodstuff or food supplement for man and animals. Of particular interest in this connection are micro-organisms which are capable of utilising gaseous organic compounds containing one or more carbon atoms in their molecules, for example methane.

SUMMARY OF THE INVENTION

The present invention provides an improved process for the cultivation of methane-utilising micro-organisms.

PREFERRED EMBODIMENT

Accordingly the invention provides a process for the production of micro-organisms in which a methane-utilising micro-organism which is a strain of Methylomonas is grown under aerobic conditions in a liquid growth medium comprising assimilable sources of nitrogen and essential mineral salts, in the presence of methane gas and in the presence of (a) one or more methanol-utilising micro-organisms which is/are capable of metabolising methanol produced by the growing methane-utilising micro-organism, and (b) one or more non-methylotropic micro-organisms which is/are capable of metabolising organic substances produced by the methane and/or methanol utilising micro-organisms.

The term "micro-organism" is used herein in a broad sense to include not only bacteria, but also yeasts, filamentous fungi, antinomycetes and protozoa.

It has been found by the Applicant that in the above-mentioned mixed culture of micro-organisms there is a synergistic effect resulting in a higher growth rate and yield of micro-organisms than when the methane-utilising micro-organism is grown alone or when methane- and methanol-utilising micro-organisms are grown together. Certain other advantages are obtained in processes using such mixed cultures including an increased resistance to infection and reduced foam production compared with processes using only one species of micro-organism.

Methanol is known to be an intermediate metabolite of microbial methane utilisation and as such may be present in culture medium during the growth of methane-utilising bacteria. Thus, the presence of methanol-utilising micro-organisms in addition to the methane-utilising bacterium may presumably increase the yield of micro-organism from a given weight of methane by giving a more complete conversion of the methane to biomass, and indeed this has been confirmed by the Applicant. The yield was further increased in the presence of the third group of (non-methylotrophic) micro-organisms. This observation may be explained as follows: The non-methylotrophic organisms utilise organic substances produced during the metabolism of methane and methanol and thereby increase the yield of biomass, remove inhibitory metabolites and produce growth promoting molecules. Mixed cultures for use in the process of the invention may be obtained in one of two ways:

a. Mixed cultures comprising a methane-utilising micro-organism in association with a number of methanol-utilising micro-organisms and a smaller number of non-methylotrophic micro-organisms may be isolated from natural sources. A particularly preferred mixed culture designated T3 in the Examples (and having the NCIB Accession No. 11085) has been isolated and found to comprise a methane-utilising micro-organism characterized by stacked membranes and designated SM3 (NCIB 11084), a methanol-utilising micro-organism of a new species designated OML (NCIB 11112) and four non-methylotrophic micro-organisms designated $M_1$, $M_2$, $M_3$ and $M_4$ in the Examples. Organism $M_1$ is a species of Pseudomonas (NCIB 11062), organism $M_2$ is a species of Mycobacterium (NCIB 11061), organism $M_3$ is a species of Pseudomonas (NCIB 11063) and $M_4$ is a species of Pseudomonas (NCIB 11065).

b. Suitable mixed cultures may also be obtained by combining one or more strains of Methylomonas with one or more strains of methanol-utilising micro-organisms and one or more strains of non-methylotrophic micro-organisms.

Examples of suitable methanol-utilising micro-organisms are strains of Hyphomicrobium (for example NCIB No. 11040), *Pseudomonas extorquens* and *Pseudomonas methylotropha* (for example NCIB Nos. 10,508 – 10,515 and 10,592 – 10,596). Examples of suitable non-methylotrophic micro-organisms include strains of Pseudomonas (for example NCIB Nos. 11019 and 11022), Acinetobacter (for example NCIB No. 11020), Curtobacterium (for example NCIB No. 11021), Mycobacteriaceae and Achromobacteriaceae.

The before-mentioned mixed culture T3 (NCIB 11085) and the strains SM3 (NCIB 11084), OML (NCIB 11112), $M_1$(NCIB 11062), $M_2$(NCIB 11061), $M_3$(NCIB 11063), and $M_4$(NCIB 11065) are all novel micro-organisms and accordingly the invention also provides these novel organisms as well as a process for the production of micro-organisms in a liquid growth medium in which one or more of these micro-organisms are employed.

The liquid growth medium also comprises a nitrogen-containing compound which may be ammonia, urea, an ammonium salt such as the sulphate chloride or a nitrate, for example an alkali metal nitrate. The compound is suitably present in a concentration from 3–50 g/l.

Other elements which may be present in the medium are phosphorus, sulphur, magnesium and iron. The phosphorus source is preferably one or more phosphates, for example $K_2HPO_4$, $KH_2PO_4$, $Na_2HPO_4$ or $(NH_4)_2HPO_4$, or phosphoric acid, preferably present in a concentration from 3–20 g/l. The sulphur source may be sulphuric acid or a sulphate such as $(NH_4)_2SO_4$ suitably in a concentration from 0.5–5.0 g/l. The two metals are provided as one or other of their salts, for example $MgSO_4.7H_2O$ in a concentration from 0.2–2.0 g/l and $FeCl_3.6H_2O$ in a concentration from 0.01–0.1 g/l.

The medium may also contain trace amounts of other elements in the form of suitable salts, for example calcium, manganese, zinc, cobalt, molybdenum and boron. Examples of suitable media are given in the examples.

The process of the invention may be carried out batch-wise, semi-continuously but preferably in continuous flow culture. To obtain growth the micro-organisms are inoculated into the medium which is contacted with a gas mixture containing methane and oxygen. Methane may be supplied in the form of natural gas. For continuous flow culture the micro-organisms may be grown in any suitably adapted fermentation vessel, for example a stirred baffled fermenter or sparged tower fermenter, which is provided either with internal cooling or an external recycle cooling loop. Fresh medium is pumped continuously into the culture at rates equivalent to 0.02 to 1.00 culture volumes per hour and culture is removed at a rate such that the volume of culture remains constant. A gas mixture containing methane and oxygen and possibly carbon dioxide or other gases is contacted with the medium preferably by bubbling continuously through a sparger at the base of the vessel. The source of oxygen for the culture may be air, oxygen or oxygen enriched air. Spent gas is removed from the head of the vessel. Spent gas may be recycled either through an external loop or internally by means of a gas inducer impeller. The gas flows and recycle should be arranged to give maximum growth of organism and maximum utilisation of methane.

The temperature of the culture is generally maintained between 30° to 50° C and preferably from 38° to 45° C. The pH of the culture is controlled at a pH between 6.0 and 8.0 and preferably between 6.4 and 7.4 by the appropriate addition of an alkali, for example NaOH, KOH, NH$_4$OH, and/or an acid, for example H$_2$SO$_4$ or H$_3$PO$_4$.

The micro-organism cells may be harvested from the growth medium by any of the standard techniques commonly used, for example flocculation, sedimentation, and/or precipitation, followed by centrifugation and/or filtration. The biomass is then dried e.g. by freeze or spray drying and may be used in this form as a protein food stuff or food supplement for man or animals. The invention is illustrated further in the following examples.

EXAMPLE 1

Isolation of Cultures of bacteria growing on methane

A mixed culture of bacteria which grows on methane was isolated from a mud sample taken from a tropical duck farm. Two grammes of the sample were put into a 250 ml shake-flask containing 25 ml of 1SM medium (described in example 3) and gassed twice daily with a gas mixture consisting of 25 percent methane and 75 percent air. The flask was incubated on a rotary shaker of orbital radius 2.5 cm at 200 rpm for one week. The culture in which turbidity had developed was sub-cultured, using 2 ml of inoculum, into similar shake-flasks observing aseptic precautions. This was repeated several times and when reproducible good growth was obtained the shake-flask culture was used to inoculate a fermenter of the type described in Example 5. The characteristics of the culture, designated T3, are described in detail in Example 2.

EXAMPLE 2

Microbiological characteristics of the culture T3

1. The culture consists of an obligate methane-utilising bacterium designated SM3 (NCIB 11084) growing in association with a methanol-utilising bacterium and species of non-methylotrophic bacteria. The methane-utilising organism SM3 (NCIB 11084) has a somewhat variable morphology, appearing as short rods or cocci rods, and has an internal membrane structure arranged in parallel stacks in the cell. This organism grows only weakly alone on methane. On the basis of the above description the organism appears to be a previously undescribed species of a Methylomonas type (NCIB 11084).

2. The methanol-utilising organism designated OML (NCIB 11112) is characterised by its ability to grow and form colonies only on agar plates containing methanol as the sole carbon source. No growth occurs in the presence of glucose, lactose, sucrose, mannitol, inositol, citrate or nutrient agar. The organism is approximated 2$\mu$ long and 1$\mu$ wide, with a single polar flagellum. Colonies on agar are smooth and grey with an entire margin, appearing on methanol/mineral salts agar plates after incubation for 2 days at 42° C. On the basis of the above description the organism appears to be a previously undescribed species of a Pseudomonas type NCIB 11112).

3. Other types of organism were isolated from the mixture which would grow neither on methane nor methanol as the only carbon source. These were designated $M_1$, $M_2$, $M_3$ and $M_4$. These were submitted to standard tests in order to determine to which general of micro-organisms they belonged.

The tests used have previously been described in such standard works as a. "Manual for the Identification of Medical Bacteria", S. T. Cowan and K. J. Steel, Cambridge University Press (1966)
b. "Bergey's Manual of Determinative Bacteriology," 7th Edition, Williams and Wilkins (1959)
c. "A Guide to the Identification of the General of Bacteria", V. B. D. Skerman, 2nd Edition, Williams and Wilkins (1967). For some these tests alternative procedures are available and further brief details are given below to indicate the test method actually used in these cases.

Oxidase test - Kovacs, 1956
Indole production - Kovacs reagent, 1928
Voges-Proskauer test - Barritt, 1936
Urease production - Oxoid media, Christensen medium, 1946
Citrate utilisation - growth on Simons citrate slopes, confirmed in Koser's broth.

The results of these tests are shown in Tables 1 and 2.
From the results of these tests the following conclusions can be drawn as to the identity of the organisms:

Organism $M_1$ is a species of Pseudomonas (NCIB 11062). Organism $M_2$ is a species of Mycobacterium (NCIB 11061). Organism $M_3$ is a species of Pseudomonas (NCIB 11063). Organism $M_4$ is a species of Pseudomonas (NCIB 11065).

TABLE 1

IDENTIFICATION OF NON-METHANE UTILISING BACTERIA PRESENT IN MIXED CULTURE T3 - FIRST STAGE TESTS

| TEST | $M_1$ | $M_2$ | $M_3$ | $M_4$ |
|---|---|---|---|---|
| GRAM STAIN | − | + | − | − |
| SHAPE | rod | rod | rod | rod |
| SPORES FORMED | − | − | − | − |
| MOTILE | + | − | + | + |
| | (by means of polar flagella) | | (by means of polar flagella) | (by means of polar flagella) |
| CATALASE PRODUCTION | + | + | + | + |
| OXIDASE | + | − | + | + |

TABLE 1-continued

IDENTIFICATION OF NON-METHANE UTILISING BACTERIA
PRESENT IN MIXED CULTURE T3 - FIRST STAGE TESTS

| TEST | $M_1$ | $M_2$ | $M_3$ | $M_4$ |
|---|---|---|---|---|
| ACTIVITY | | | | |
| GLUCOSE UTILIZATION (acid) | − | − | − | − |
| O - F test (Hugh & Leifson) | − | − | Oxidative | Oxidative |
| ACID FAST | | non-acid fast | | |

TABLE 2

IDENTIFICATION OF NON-METHANE UTILISING BACTERIA PRESENT
IN MIXED CULTURE T3 - SECOND STAGE TESTS

| TEST | $M_1$ | $M_2$ | $M_3$ | $M_4$ |
|---|---|---|---|---|
| UREASE ACTIVITY | − | + | − | + |
| CITRATE UTILIZATION | + | − | + | + |
| GELATIN HYDROLYSIS | + | − | + | + |
| INDOLE PRODUCTION | − | − | − | − |
| MR (methyl red) & VP (Voges-Proskauer) REACTIONS | − | − | − | − |
| GLUCOSE (ACID PRODUCTION) | − | − | − | − |
| LACTOSE (ACID) | − | − | − | − |
| SUCROSE (ACID) | − | − | − | − |
| MANNITOL (ACID) | − | − | − | − |
| MALTOSE (ACID) | − | − | − | − |
| GROWTH ON NUTRIENT AGAR | + | + | + | + |
| CATALASE ACTIVITY | + | + | + | + |
| REDUCTION OF NITRATE | − | weak | weak | − |

EXAMPLE 3

Cultures were grown from mixtures of the following bacteria:

| | |
|---|---|
| SM3 | (grows only on methane) |
| OML | (grows only on methanol) |
| $M_1$ | (a non-methylotrophic bacterium) |
| $M_2$ | (a non-methylotrophic bacterium) |
| $M_3$ | (a non-methylotrophic bacterium) |
| $M_4$ | (a non-methylotrophic bacterium) |

A feed medium based on that described by Sheehan & Johnson (hereinafter referred to as medium ISM) was prepared which contained the following ingredients:

| | |
|---|---|
| $KH_2PO_4$ | 1.6 grams/liter |
| $Na_2HPO_4$ | 1.16 grams/liter |
| $NaNO_3$ | 1.18 grams/liter |
| $MgSO_4 \cdot 7H_2O$ | 0.08 grams/liter |
| $FeSO_4 \cdot 7H_2O$ | 0.014 grams/liter |
| $Ca(NO_3)_2 4H_2O$ | 0.025 grams/liter |
| $CuSO_4 \cdot 5H_2O$ | $8 \times 10^{-6}$ gram/liter |
| $ZnSO_4 \cdot 7H_2O$ | $6.8 \times 10^{-7}$ gram/liter |
| $MnSO_4 \cdot 4H_2O$ | $6.0 \times 10^{-7}$ gram/liter |
| $Na_2NoO_4 \cdot 2H_2O$ | $4.8 \times 10^{-7}$ gram/liter |

Cultures were grown in sterile glass vessels of 500ml volume through which a continuous supply of methane/air mixture was bubbled.

The apparatus consisted of a series of vessels through which a methane (25%)/air (75%) mixture was bubbled via a sintersol filter. The apparatus openings allowed inoculation and sampling of the culture.

The flasks were inoculated with 1.5 ml of a fresh culture (24 hrs old) of each of the 4 organisms designated $M_1$, $M_2$, $M_3$ & $M_4$. 4 mls of both the methane-utilising (SM3) and methanol-utilising (OML) bacteria were added from 2–3 days old cultures grown in shake flasks on ISM medium.

The medium in the vessels was 400 ml of ISM medium described above and growth was assessed by measuring optical density (OD) at 625 nM wavelength.

The results are given in Table 3. These results show that a mixed culture is necessary for best growth on methane. The situation is improved slightly by the presence of the methanol utiliser but for best growth all constituents are required.

Table 3

Growth obtained on methane after 3 days using various combinations of the bacteria present in culture T3

| Organisms present in inoculum | Amount of Growth (optical Density units after 3 days) |
|---|---|
| SM3 | 0.14 |
| SM3, OML | 0.25 |
| SM3, $M_1$, $M_2$, $M_3$, $M_4$ | 0.27 |
| SM3, OML, $M_1$, $M_3$, $M_4$ | 0.59 |

These results are the mean values from 3 experiments each being 2 or 3 replicates.

These results are the mean values from 3 experiments each being 2 or 3 replicates.

EXAMPLE 4

The following experiments were designed to see if the components of culture T3 could be replaced by other micro-organisms having similar functions. Cultures in bubbled glass vessels were set up as in example 3, but in some cases the methanol-utiliser from culture T3 was replaced by the methanol-utilising organism NCIB 11040. Similarly the non-methylotrophic components of T3 were replaced by the non-methylotrophic organisms NCIB Nos. 11019, 11020, 11021 and 11022. The results of these experiments are shown in Table 4.

Table 4

Increase in Optical Density (at 625nM) of various mixed cultures growing on methane
(mean values of 2 experiments, each with 4 replicates per culture)

| Methane utiliser (SM3) | Methanol utiliser (OML) | Methanol utiliser (NCIB No 11040) | Non-methylotrophic organisms M1, M2, M3 & M4 | Non-methylotrophic organisms (NCIB Nos 11019–11022) | OD at 625nM After 3 days |
|---|---|---|---|---|---|
| + | + | − | + | − | 0.53 |
| + | − | + | + | − | 0.56 |
| + | − | + | − | + | 0.57 |

+ = present in the culture
− = absent in the culture

The difference between figures in vertical columns in Table 6 is not significant. It can therefore be concluded that the methanol utilising organism NCIB No. 11040 may be substituted for OML. Similarly, the non-methylotrophic components are interchangeable.

EXAMPLE 5

Fermentations using culture T3

The culture was grown in continuous culture on mineral medium, methane and air. A Biotec fermenter of working volume 2.5 liters was used. Methane and air were sparged into the liquid contents at a rate of 150 ml/min and 450 ml/min respectively. The temperature of the medium was controlled at 42° C and the pH at 7.4 by the automatic addition of 2N NaOH. The medium was stirred at a rate of 1,000 rpm and the operating pressure of the fermenter was only slightly above atmospheric pressure.

The liquid medium designated SJ4 used for continuous culture had the following composition:

| | |
|---|---|
| $KH_2PO_4$ | 1.6 g/l |
| $Na_2HPO_4$ | 1.16 g/l |
| $NaNO_3$ | 3.18 g/l |
| $MgSO_4 \cdot 7H_2O$ | 0.107 g/l |
| $FeSO_4 \cdot 7H_2O$ | 0.009 g/l |
| $Ca(NO_3)_2 \cdot 4H_2O$ | 0.06 g/l |
| Trace element solution | 1 ml/l |
| Conc. sulphuric acid | 0.33 ml/l |
| Distilled water to 1 liter | |

The trace element solution used to make up the medium had the following composition:

| | |
|---|---|
| $CuSO_4 \cdot 5H_2O$ | 3 g/l |
| $ZnSO_4 \cdot 7H_2O$ | 0.336 g/l |
| $MnSO_4 \cdot 4H_2O$ | 0.5 g/l |
| $NaMoO_4 \cdot 2H_2O$ | 0.213 g/l |
| $CoCl_2 \cdot 6H_2O$ | 0.015 g/l |

This stock solution was added to the rest of the medium at a concentration of 1 ml/l as mentioned above.

The fermenter was first filled with 2 liters of ISM medium (see example 1) stirred, aerated and supplied with methane as described above. It was inoculated with 100 ml of fully grown shake flask culture T3. Once growth had taken place in the fermenter, medium SJ4 was fed into with a dilution rate of 0.08 $h^{-1}$. This was increased in steps of 0.02 $h^{-1}$ at 2 day intervals up to 0.22 $h^{-1}$ without the culture washing out. Steady states were obtained in which the biomass concentration was from 2.5 to 6 $gl^{-1}$. This in no way represents the highest biomass concentration obtained in continuous culture. The culture was maintained in continuous culture for more than 3 thousand hours. Organisms were harvested and subjected to analysis, the results of which are shown in subsequent examples.

At any steady state a particular dilution rate in continuous culture the proportion of the total population of bacteria represented by any one bacterial species did not change. Also the culture was very resistant to infection by foreign micro-organisms, so that no contamination could be detected even when the culture was deliberately infected with foreign organisms.

EXAMPLE 6

A mixed culture of methane-utilising bacteria was grown in continuous culture in a 300 l fermenter under conditions essentially equivalent to those described for the small-scale fermentation. The cells were harvested by centrifugation and spray dried. A free flowing colourless, odourless, powder (SCP) was obtained, consisting of dry bacterial cells. It has a protein content of e. 78 percent (calculated as N × 6.25). The nutritional quality of the powder was tested in rat feeding trials as follows:

SCP was fed to weanling rats in 10 day trials so that SCP formed the only protein source in the diet. In each trial a control diet which contained casein as the sole protein source was included. Herring meal, one of the richest forms of animal feed supplement, was also fed to rats for comparison. The crude protein level, (N × 6.25) in each diet was 10 percent but all other nutrients were provided in amounts adequate for optimum growth. The results of the feeding trial are shown in Table 5.

Table 5

| Dietary constituent | Feed conversion efficiency | Protein efficiency ratio |
|---|---|---|
| Casein | 0.243 | (2.50) |
| SCP | 0.256 | 2.59 |
| Herring meal | 0.233 | 2.2 |

From Table 5, it can be seen that SCP produced from a mixed culture of bacteria growing on methane is a satisfactory form of protein supply. Indeed, it is better than fish meal as a dietary constituent for animal feed.

The amino-acid spectrum of the SCP was analysed and the results are shown in Table 6. These results indicate that the amino-acid balance is such that the SCP is very suitable as an animal protein feed.

TABLE 6

Amino-acid content of SCP

| Amino acid | % crude protein (g/16g N) |
|---|---|
| Aspartic Acid | 8.48 |
| Threonine | 4.00 |
| Serine | 3.30 |
| Glutamic Acid | 9.96 |
| Proline | 4.18 |
| Glycine | 4.63 |
| Alanine | 6.16 |
| Valine | 5.91 |
| Cystine (½) | 0.31 |
| Methionine | 2.78 |
| Isoleucine | 4.50 |
| Leucine | 7.02 |
| Tyrosine | 3.51 |
| Phenylalanine | 4.37 |
| Ammonia | 2.09 |
| Ornithine | 0.16 |
| Lysine | 5.43 |
| Histidine | 2.00 |
| Arginine | 5.84 |
| N % m/m | 11.4 |
| Crude Protein (% dry wt.) | 71.25 |

The invention claimed is:

1. A process for the production of micro-organisms in which a methane-utilising micro-organism which is a strain of Methylomonas having the NCIB Accession No. 11084 is grown under aerobic conditions in a liquid growth medium comprising assimilable sources of nitrogen and essential mineral salts, in the presence of methane gas and in the presence of (a) a methanol-utilising micro-organism having the NCIB Accession No. 11112 which is capable of metabolizing methanol produced by the strain of Methylomonas, and (b) one or more non-methylotrophic micro-organisms selected from the group of species comprising Pseudomonas having the NCIB Accession No. 11062, Mycobacterium having the NCIB Accession No. 11061, Pseudomonas having the NCIB Accession No. 11063 and Pseudomonas having the NCIB Accession No. 11065 which is/are capable of metabolising organic substances produced during the metabolism of methane and/or methanol.

2. A process according to claim 1, wherein the methane-utilising micro-organism, the methanol-utilising micro-organism and the non-methylotrophic micro-organisms are employed in a mixed culture designated T3 and having the NCIB Accession No. 11085.

3. A process according to claim 1, wherein the temperature is maintained in the range 38°– 45° C.

4. A process according to claim 1, wherein the pH is controlled in the range 6.4 – 7.4.

* * * * *